US012589846B2

(12) United States Patent
Sieber

(10) Patent No.: US 12,589,846 B2
(45) Date of Patent: Mar. 31, 2026

(54) GAS DISTRIBUTOR FOR REBREATHER SUPPORTING CLOSED AND OPEN CIRCUIT MODES

(71) Applicant: Oxygen Scientific GmbH, Graz (AT)

(72) Inventor: Arne Sieber, Graz (AT)

(73) Assignee: OXYGEN SCIENTIFIC GMBH, Graz (AT)

( * ) Notice: Subject to any disclaimer, the term of this patent is extended or adjusted under 35 U.S.C. 154(b) by 1033 days.

(21) Appl. No.: 17/581,530

(22) Filed: Jan. 21, 2022

(65) Prior Publication Data

US 2022/0234703 A1 Jul. 28, 2022

(30) Foreign Application Priority Data

Jan. 25, 2021 (DE) ..................... 10 2021 101 549.9

(51) Int. Cl.
*B63C 11/14* (2006.01)
*A61M 16/00* (2006.01)
(Continued)

(52) U.S. Cl.
CPC ......... *B63C 11/14* (2013.01); *A61M 16/0045* (2013.01); *A61M 16/201* (2014.02);
(Continued)

(58) Field of Classification Search
CPC .... B63C 11/14; B63C 11/24; A61M 16/0045; A61M 16/201; A61M 16/209; A62B 18/04; A62B 18/19; A62B 19/00
See application file for complete search history.

(56) References Cited

U.S. PATENT DOCUMENTS 2,485,039 A 10/1949 Cousteau et al.
2,747,572 A 5/1956 Gagnan
(Continued)

FOREIGN PATENT DOCUMENTS

DE 202015106233 U1 * 3/2016 .............. A62B 9/02
EP 2207715 A1 7/2008
(Continued)

OTHER PUBLICATIONS

Machine English translation of DE-202015106233-U1. (Accessed on Dec. 16, 2024). (Year: 2016).*
(Continued)

*Primary Examiner* — Kendra D Carter
*Assistant Examiner* — Maap Ellabib
(74) *Attorney, Agent, or Firm* — Womble Bond Dickinson (US) LLP

(57) ABSTRACT

A gas distributor for a rebreather, the gas distributor being configured for connection with an inhale hose and with an exhale hose with a mouthpiece in between, wherein the gas distributor comprises a gas distributor housing, an inhale chamber at the gas distributor housing and comprising a first inhale port for connection with an inhale counterlung or with a scrubber, a second inhale port for connection with the inhale hose, and a gas supply valve for supplying gas on demand, an exhale chamber at the gas distributor housing and comprising a first exhale port for connection with an exhale counterlung or with a scrubber, a second exhale port for connection with the exhale hose, and an overpressure valve for opening in an event of overpressure, and a switch arranged at the gas distributor housing and configured for being switchable between an open circuit mode and a closed circuit mode.

18 Claims, 7 Drawing Sheets

(51) Int. Cl.

| | |
|---|---|
| *A61M 16/20* | (2006.01) |
| *A61M 16/22* | (2006.01) |
| *A62B 18/04* | (2006.01) |
| *A62B 18/10* | (2006.01) |
| *A62B 19/00* | (2006.01) |

(52) U.S. Cl.

CPC .......... *A61M 16/209* (2014.02); *A61M 16/22* (2013.01); *A62B 18/04* (2013.01); *A62B 18/10* (2013.01); *A62B 19/00* (2013.01)

(56) References Cited

U.S. PATENT DOCUMENTS

| | | | | |
|---|---|---|---|---|
| 5,127,398 | A | 7/1992 | Stone | |
| 8,770,192 | B2 | 7/2014 | Tham | |
| 8,770,195 | B2 * | 7/2014 | Stone | B63C 11/24 |
| | | | | 128/205.24 |
| 2008/0276942 | A1 * | 11/2008 | Gurr | A62B 7/10 |
| | | | | 128/205.28 |
| 2010/0043797 | A1 * | 2/2010 | Deas | B63C 11/186 |
| | | | | 128/205.24 |
| 2015/0251026 | A1 | 9/2015 | Gradischar | |
| 2016/0016020 | A1 * | 1/2016 | Sieber | A62B 18/08 |
| | | | | 128/205.12 |

FOREIGN PATENT DOCUMENTS

| | | | | | |
|---|---|---|---|---|---|
| GB | 2 340 760 | A | | 3/2000 | |
| GB | 2 462 672 | A | | 2/2010 | |
| GB | 2511090 | A | * | 8/2014 | ............ A62B 18/08 |
| GB | 2 531 137 | A | | 4/2016 | |
| WO | 2007/126317 | A1 | | 11/2007 | |
| WO | 2009/058080 | A1 | | 5/2009 | |
| WO | 2014056009 | A1 | | 4/2014 | |

OTHER PUBLICATIONS

European Search Report for Application No. 22152980.3, dated Jun. 29, 2022, 9 pages.

* cited by examiner

GAS DISTRIBUTOR FOR REBREATHER SUPPORTING CLOSED AND OPEN CIRCUIT MODES

CROSS-REFERENCE TO RELATED APPLICATION(S)

This application claims priority to German Patent Application Number 10 2021 101 549.9, filed on Jan. 25, 2021, the entire content of which is incorporated herein by reference.

FIELD OF THE INVENTION

The invention relates to a gas distributor for a rebreather, a rebreather for supplying a user with breathing gas, and a method of wearing a rebreather by a user.

Technological Background

A breathing apparatus is used whenever a person is exposed to a life threatening or non-life sustaining environment. A major part of a life supporting system is the breathing apparatus supplying breathing gas when an individual is exposed, for example, to water (such as during diving) or to hazardous gases (for instance for firefighting). The gas supply system may be built around tanks with compressed gas. A regulator system may reduce the pressure from the tanks to ambient pressure. An individual may breath normally via an "on demand" valve, which may provide fresh breathing gas from the tank, whenever the person inhales. Such systems may be denoted as open circuit (OC) breathing systems, as the exhaled gas may be vented through another valve into the environment.

Open circuit breathing systems used in SCUBA (Self-Contained Underwater Breathing Apparatus) diving may comprise a gas supply tank (for example 200-300 bar compressed breathing gas), a pressure regulator and a demand valve with a diaphragm to reduce the pressure of the breathing gas supply to ambient pressure so that it can be inhaled safely. The "on demand" valve may comprise a valve element and a diaphragm. When the diver inhales, a negative pressure may be created inside a mouthpiece. This negative pressure may act on the diaphragm, which further exerts a force on and actuates a lever of a gas valve so that gas is injected. The pressure threshold at which gas is getting injected may be denoted as cracking pressure. In open circuit breathing systems this cracking pressure may be set to −1 to −3 mbar.

There are two types of open circuit breathing systems. The first and most frequently used type, the single hose regulator, may comprise a pressure regulator mounted on the tank, which reduces the tank pressure to a pressure of typically 8-10 bar over ambient pressure which is equal to the surface atmospheric pressure plus the hydrostatic pressure. This pressure regulator may be denoted in diving as first stage. Moreover, an "on demand" valve may form part of a single hose regulator, which provides breathing gas to the diver. This device may be denoted as "second stage". A downstream OC valve is an example for such "on demand" valves. The first and the second stage are connected with a medium pressure hose.

U.S. Pat. No. 2,747,572 A discloses a single hose regulator.

The second type of open circuit breathing system is the dual or double hose regulator: In such a dual or double hose regulator, an "on demand" valve with diaphragm and pressure regulator may be mounted on the top of the tank and may thus be located close to the neck of the diver. One inhale hose is leading from the "on demand" valve to the inhale side of a mouthpiece. One exhale hose is leading from the exhale side of the mouthpiece back to the location of the "on demand" valve, where exhaled gas may be vented into the ambient through an exhale valve. In a dual or double hose regulator, two direction valves may be located inside the body of the mouthpiece to assure a correct gas flow, avoid pendulum breathing and reduce carbon dioxide ($CO_2$) buildup.

U.S. Pat. No. 2,485,039 A discloses a dual hose regulator.

The amount of time within which an open circuit diving system can provide breathing gas may depend on the amount of gas stored in the tanks, the gas volume used in every breath and the respiratory rate. Typical breathing volumes (RMV, respiratory minute volume) are 5-10 l/min RMV at rest. During light activities, the RMV may be around 12-15 l/min. During moderate exercise, the RMV can rise up to 40-60 l/min. As only a small portion of the breathing gas is metabolized (in fact only 0.3-0.8 l/min oxygen ($O_2$) at rest and up to 3.5 l/min $O_2$ under heavy work are taken up by the human body), the gas efficiency of open circuit systems is quite low, for example only about 3%. Especially when it comes to diving, where the ambient pressure is increased by 1 bar each 10 m depth due to the additional hydrostatic pressure, the efficiency may even decrease and may reach values of about 0.6% at 40 m depth. To enable deep and long dives, a sufficient gas supply is required, including in many cases several tanks resulting in bulky and cumbersome equipment.

Closed circuit (CC) rebreathers may have advantages in comparison to open circuit systems. In an oxygen rebreather, a person may exhale into a bag—the so called counterlung. A scrubber may remove carbon dioxide, and fresh gas may be added to replace metabolized oxygen. This recycled gas may then be inhaled by the diver again. In the case of an $O_2$ rebreather, the circuit may contain mainly $O_2$ and traces of nitrogen ($N_2$). Thus, the partial pressure of $O_2$ ($pO_2$) inside the circuit is dependent on the ambient pressure (Dalton's Law). Such a system has the advantage of increasing the gas efficiency up to almost 100%. $O_2$ rebreathers can be designed as purely mechanical systems, and may be robust and reliable. Rebreathers may require a mixture of oxygen and other gases for respiration. For example in the case of firefighting, it may be desirable to avoid breathing systems containing pure $O_2$ because of the increased risk of combustion. In diving applications, the use of pure oxygen may be only advisable to a maximum depth of 6 m, as $O_2$ becomes toxic at partial pressures greater than 1.4-1.6 bar. In diving, a diluent gas may be used to lower the partial pressure of $O_2$. This diluent gas may be air, or a breathing gas called TRIMIX, containing helium (He), $O_2$ and $N_2$.

Closed circuit rebreather (CCR) systems that use a gas mixture are not purely mechanical since in that case $pO_2$ monitoring and regulation may be carried out. Wet electrochemical $pO_2$ sensors may be used to measure $pO_2$. A manual or automatic control loop may be used to keep the $pO_2$ at constant level by replacing metabolized $O_2$ with fresh $O_2$ from a supply tank.

A rebreather may comprise a mouthpiece with direction valves. Such mouthpieces may have an integrated mechanism to close the valve when the diver is not using it to avoid water ingress. Such mouthpieces may be denoted as dive surface valve (DSV). Furthermore, an inhale hose and an exhale hose may be provided which may lead to a counterlung. More specifically, an exhale counterlung or an inhale counterlung may be provided. It is also possible that a rebreather comprises an exhale counterlung and an inhale counterlung. A scrubber canister may be provided in which a $CO_2$ filter may be housed. Furthermore, a hose connection may be formed between the scrubber canister and the counterlungs. A manual loop volume valve (MLV) or automatic loop volume valve (ALV) may be provided as well. In mix gas rebreathers, a corresponding valve may be denoted as manual diluent or automatic diluent valve (ADV). Furthermore, a loop overpressure valve may be provided. A sensor and an electronic compartment may be arranged on top of the scrubber canister. Furthermore, a handset to display dive relevant data and a head-up display (HUD) may be provided.

When the diver descends, the loop volume may be decreased due to the increasing ambient pressure. This can be compensated with an injection of gas, as the breathing volume remains the same independent on the depth of the diver. For this reason, rebreathers may be equipped with a manual valve, which may allow injection of gas into the loop. Alternatively, rebreathers may be equipped with an automatic loop volume valve (ALV), which works similar to a second stage OC breathing regulator—it may automatically inject gas in the loop as soon as the loop is empty and there is a negative pressure in respect to ambient. For example, the pressure threshold at which the gas injection is started may be set to −10 to −40 mbar. ALVs in closed circuit oxygen rebreathers may be supplied with pure oxygen. ALVs used in closed circuit rebreathers for deep diving may be supplied with diluent gas. Therefore, such valves may be denoted as auto diluent valve (ADV).

The term ALV will be used in the following and in order to address both oxygen rebreathers and deep diving or mix gas closed circuit rebreathers.

The loop pressure inside a rebreather may be dependent on the position of the counterlungs and on the divers angular position (such as pitch and roll). A depth and thus pressure difference between gas centroid of the counterlungs and centroid of the diver's lung may be denoted as hydrostatic imbalance.

An ALV in a rebreather may be set to a high negative cracking pressure in order to avoid unwanted gas injections in some positions, where the ALV is deeper than the centroid of the gas volume in the counterlungs. This is for example the case when a diver with an ALV located on the mouthpiece and counterlungs on the back is in a "head down" position. Without an elevated negative cracking pressure, an ALV might inject gas until the pressure is equal to the pressure at the diaphragm of the ALV. A disadvantage of an elevated cracking pressure is that it may require more physiological effort during inhalation from empty or partially empty counterlungs, as the elevated cracking pressure has to be overcome by the breathing muscles. This may be problematic in particular when the diver is in a head up position where the head is at a shallower depth than the lungs, which may result in an additional negative pressure loading on the ALV located on the mouthpiece.

When the diver ascends, the volume of the gas in the loop may increase due to the decreasing ambient pressure. An overpressure valve may be located in the loop in order to release excessive gas. Such a valve may be set to a value of +10 to +40 mbar.

A CCR may be also equipped with one or more $pO_2$ sensors to monitor the $pO_2$ inside the loop. The $pO_2$ values may be shown on a display. A rebreather may also have an additional head-up display, which may be located on the rebreather mouthpiece in a position where it is always in the field of view of the diver. These may be basic displays consisting of one or more light emitting diodes (LEDs).

In the case of a malfunction of the rebreather, the $pO_2$ inside the loop can quickly reach values outside life sustaining thresholds. In such cases the HUD warns the diver which may then "bail out" as first response. Under "bail out", it may be understood that breathing continues from an OC second stage regulator.

In order to facilitate changing from closed circuit breathing (CCR) to open circuit breathing mode (OC), a rebreather mouthpiece may feature two different modes—one CCR mode, in which the diver breathes from the closed circuit rebreather, and an OC mode. To realize an OC function, parts of a second stage regulator may be integrated into the mouthpiece (in particular diaphragm, diaphragm actuated valve, exhaust valve). The diver may switch between the two modes by rotating a barrel inside the mouthpiece. Rebreather mouthpieces with CCR and OC mode may be denoted as bail out valves (BOV).

U.S. Pat. No. 5,127,398 discloses a rebreather mouthpiece which can be switched between open circuit and closed circuit mode.

WO 2007/126317 discloses a rebreather mouthpiece with OC and CCR mode but additional automatic loop volume valve (ALV). The cracking pressure of the ALV is not increased, instead the gas path is restricted. This does not give the same result as an increased cracking pressure, thus the ALV may free flow in some rebreather designs (especially in designs with back mounted counterlungs).

GB 2,340,760 discloses a rebreather mouthpiece with OC and CCR mode but also with an ALV. However, here the cracking pressure of the ALV is not increased.

GB 2,462,672 discloses a rebreather mouthpiece which can be switched between OC and CCR mode and has additionally an integrated ALV function. The cracking pressure is automatically adjusted to a higher pressure in CCR mode by changing the membrane active area, the leverage ratio of the diaphragm to valve seat pressures or the valve seat spring tension.

EP 2,207,715 discloses a rebreather mouthpiece with integrated OC and CCR mode and integrated ALV. Here, the cracking pressure for the ALV is increased in comparison to the OC cracking pressure. The function therefore is realized by moving a pilot valve relative to a diaphragm. In CCR mode, the pilot valve is moved away from the diaphragm, thus a decrease of the effective diaphragm area is achieved which results in a higher negative cracking pressure.

GB 2,531,137 B discloses a rebreather mouthpiece with a closed circuit mode which comprises an inhale direction valve, an exhale direction valve, an automatic diluent valve, an overpressure valve and a switching barrel which is operable by the user to switch the mouthpiece between the two modes of operation. In the closed circuit mode a user is enabled to inhale breathing gas via the inhale direction valve and to exhale breathing gas via the exhale direction valve, and the overpressure valve opens beyond a first threshold pressure, and the automatic diluent valve provides a diluent gas beyond a second threshold pressure. In the open circuit mode, a user inhales breathing gas via the automatic diluent valve and exhales breathing gas via the overpressure valve. The overpressure valve is deactivated, or the absolute value of the first threshold pressure is reduced in the open circuit switch state, and the automatic diluent valve provides a diluent gas beyond a third threshold pressure having a smaller absolute value than the second threshold pressure.

It is still difficult to provide a rebreather system which offers a high degree of functionality while being usable in a user-friendly way.

SUMMARY OF THE INVENTION

There may be a need for a rebreather which offers a high degree of functionality while being compact and usable in a user-friendly way.

According to an exemplary embodiment of the invention, a gas distributor for a rebreather is provided, the gas distributor being configured for connection with an inhale hose and with an exhale hose with a mouthpiece in between, wherein the gas distributor comprises a gas distributor housing, an inhale chamber at the gas distributor housing and comprising a first inhale port for connection with an inhale counterlung or with a scrubber, a second inhale port for connection with the inhale hose, and a gas supply valve for supplying gas on demand, an exhale chamber at the gas distributor housing and comprising a first exhale port for connection with an exhale counterlung or with a scrubber, a second exhale port for connection with the exhale hose, and an overpressure valve for opening in an event of overpressure, and a switch arranged at the gas distributor housing and configured for being switchable between an open circuit mode and a closed circuit mode.

According to another embodiment of the invention, a rebreather for supplying a user with breathing gas is provided, wherein the rebreather comprises a gas distributor having the above mentioned features.

According to still another exemplary embodiment of the invention, a method is provided which comprises wearing a rebreather having the above mentioned features by a user so that the switch of the gas distributor is located at a chest or at a back of the user.

In the context of the present application, the term "gas distributor" may in particular denote a member or an assembly for a rebreather, which may manage distribution of breathing gas to a user of a rebreather. Such a gas distributor may have gas connections for establishing a connection with gas distributor-exterior components like an inhale hose, an exhale hose, and one more counterlungs. Indirectly, a gas distributor may be gas coupled with one or more further gas distributor-exterior components of the rebreather, such as a mouthpiece connected between the mentioned hoses, a scrubber connected between the mentioned counterlungs, etc.

In the context of the present application, the term "rebreather" may in particular denote a breathing apparatus providing breathing gas to a user. In a closed circuit mode, the rebreather may absorb carbon dioxide of a user's exhaled breath to permit the rebreathing or recycling of a substantially unused oxygen content, and unused inert content when present, of each breath, and oxygen may be added to replenish the amount metabolized by the user. In an open circuit mode of a rebreather according to an exemplary embodiment, exhaled gas may be discharged into the environment of the rebreather and new gas (in particular oxygen, TRIMIX or air) is supplied, for instance from a gas tank.

In the context of the present application, the term "open circuit mode" may in particular denote an operation mode in which the gas distributor may be filled with compressed gas (such as air, oxygen or other gas mixes) from a reservoir without recirculation of exhaled gas.

In the context of the present application, the term "closed circuit mode" may in particular denote an operation mode in which the gas distributor operates by supplementing and recirculating exhaled gas.

In the context of the present application, the term "gas distributor housing" may in particular denote a single-part or multiple-part casing of the gas distributor within and/or on which the inhale chamber and the exhale chamber with their constituents may be accommodated. Furthermore, the gas distributor housing may form gas interfaces or ports with inhale and exhale hoses as well as counterlungs and/or a scrubber.

In the context of the present application, the term "gas supply valve" may in particular denote a valve having access to a gas reservoir (such as a gas tank) for providing gas (for instance comprising oxygen) through the gas supply valve to be provided to a user via a mouthpiece of the rebreather. The gas supply valve may be normally closed and may open in the event of a trigger indicating a demand of gas.

In the context of the present application, the term "overpressure valve" may in particular denote a valve being configured for removing an overpressure within the gas distributor by opening in the event of sufficient overpressure. The overpressure valve may be normally closed and may open in the event of a trigger indicating an excessive overpressure in the gas distributor, in particular in its exhale chamber.

In the context of the present application, the term "switch" may in particular denote a member operable or actuable by a user and allowing a user-defined adjustment of the present operation mode of the rebreather, in particular open circuit mode or closed circuit mode. In particular, the switch may be operable directly or remotely (for instance with a Bowden wire or with a hydraulic or pneumatic mechanism) by muscle force of the user, or may be operated by a drive unit (such as an electric motor) which may be actuated by the user or automatically by an electronic control system.

In the context of the present application, the term "mouthpiece" may in particular denote a member of the rebreather which may be anatomically adapted to the mouth of the user and via which a user may inhale and exhale breathing gas.

In the context of the present application, the term "counterlung" may in particular denote a part of a breathing loop which is designed to change in volume by the same or a similar amount as the user's tidal volume when breathing. This lets the loop expand and contract when the user breathes, letting the total volume of gas in the lungs and the loop remain constant throughout the breathing cycle. One or two counterlungs (i.e. an inhale counterlung and/or an exhale counterlung) may be present in a rebreather, and may be coupled with a scrubber.

In the context of the present application, the term "scrubber" may in particular denote a piece of equipment of a rebreather that absorbs (for instance chemically) carbon dioxide from exhaled air of the rebreather. A scrubber may also add consumed oxygen.

According to an exemplary embodiment of the invention, a gas distributor for a rebreather is provided, wherein the gas distributor integrates an assembly of constituents being configured for supporting selectively an open circuit mode or a closed circuit mode of the rebreather. In particular, the integration of an inhale chamber and an exhale chamber being gas-connectable with a gas supply valve and an overpressure valve, respectively, and being configured with ports for selective connection with a respective counterlung or a scrubber may be accomplished by a common gas distributor housing. Also a user-actuable switch which can be selectively and intuitively switched into an open circuit mode or a closed circuit mode by a user wearing the rebreather with its gas distributor on chest or back can be arranged at the gas distributor housing. This may make it possible to provide a simple and lightweight mouthpiece which does not necessarily be adapted to specifically support an open circuit mode or a closed circuit mode. By providing the mouthpiece of a rebreather according to an exemplary embodiment of the invention with a structurally simple design, wearing the mouthpiece may be more convenient for a user as compared to a heavy and complex conventional design. Advantageously, structural components supporting selection of an open circuit mode or a closed circuit mode of the rebreather may be arranged at the gas distributor according to an exemplary embodiment of the invention. The latter may be carried at a chest or at a back of a user so that its multifunctional design including a switching mechanism does not compromise user convenience. Moreover, simplifying the mouthpiece may also allow to suppress an undesired carbon dioxide increase in dead volumes of a voluminous mouthpiece.

DETAILED DESCRIPTION OF EXEMPLARY EMBODIMENTS

In the following, further exemplary embodiments of the gas distributor, the rebreather, and the method will be explained.

A rebreather with a simple mouthpiece and a separate gas distributor which comprises components used for changing between OC and CCR mode may overcome conventional shortcoming of an integration of a second stage regulator in a mouthpiece. By arranging components for changing between the OC and the CCR modes in a gas distributor rather than in a mouthpiece may advantageously decrease the overall size as well as weight of the mouthpiece. Furthermore, a conventionally implemented medium pressure hose (to supply gas from a tank to the second stage valve) additionally to the two corrugated beathing hoses located in the mouthpiece may become dispensable according to an exemplary embodiment of the invention. Consequently, a simple rebreather mouthpiece being less bulky than conventional BOV designs may be implemented according to an exemplary embodiment of the invention. Hence, use of a rebreather with a gas distributor according to an exemplary embodiment of the invention can be comfortable for the diver and may reliably prevent fatigue of jaw muscles as well as pain of the jaw, especially when dive times are longer. Furthermore, conventional rebreather BOV mouthpieces with open circuit and closed circuit modes may use a barrel having a large diameter between 30 and 60 mm that is rotated and that is sealed with large O-rings to switch between the two modes. By omitting such large barrels (suffering from high friction caused by the O-rings) thanks to an integration of the switch in the gas distributor according to an exemplary embodiment, the effort to operate the switch may be significantly reduced.

An advantage of a gas distributor according to an exemplary embodiment of the invention is a reduction of the dimensions of the mouthpiece by omitting mouthpiece-related switching and valve arrangements. Moreover, a conventionally large dead space between direction valves of the conventionally voluminous mouthpiece may be significantly reduced according to an exemplary embodiment of the invention, which advantageously suppresses significant $CO_2$ buildup.

Furthermore, conventional rebreather mouthpieces which can be changed between CCR and OC mode, and where the components of the "on demand" valve are used as integrated ALV, may face the following issues which may be overcome by exemplary embodiments of the invention: Depending on the rebreather design, the components of the "on demand" valve may be conventionally located distant from the gas centroid of the counterlungs. To avoid unwanted gas injections into the counterlungs in certain body positions, where the ADV is located deeper than the centroid of the gas volume in the counterlungs, the cracking pressure of the ADV has to be set to an increased negative pressure. To overcome this elevated negative cracking pressure, more physiological effort is required. Unfavorable body positions, for instance head up, where the ALV is at a shallower depth than the lung centroid, leads to additional negative pressure on the ALV, thus even more physiological effort is required to overcome the negative pressure loading on a diaphragm. According to an exemplary embodiment of the invention, in which a gas supply valve is integrated in the gas distributor rather than in the mouthpiece, the physiological effort of a user wearing the rebreather can be reduced.

Moreover, the ALV function of a conventional rebreather in open circuit mode may be not functional, as the "on demand" valve is separated from the breathing loop. If the diver descends while breathing in open circuit mode, the gas in the rebreather loop (scrubber and counterlungs) gets compressed and the rebreather loop may collapse, as no gas is added to the loop. This may lead to damage of rebreather components. Even such undesirable phenomena may be reliably prevented according to an exemplary embodiment of the invention in which the gas supply valve is integrated in the gas distributor (rather than in the mouthpiece) and hence close to the breathing loop.

According to an exemplary embodiment of the invention, a gas distributor for a rebreather is provided which offers both CCR mode and OC mode, and which may provide an integrated manual loop volume valve (MLV), an automatic loop volume valve (ALV) and an overpressure valve (OPV). A rebreather with such a gas distributor may overcome at least part of the above-mentioned and/or other conventional shortcomings.

In contrast to conventional approaches providing a multifunctional rebreather mouthpiece based on the integration of one or more components including an "on demand" valve in a mouthpiece, exemplary embodiments of the invention provide a rebreather which is based on the gist of combining an assembly comprising an inhale hose, an exhale hose and a simple and lightweight mouthpiece from a double hose regulator or rebreather (DSV) with a multifunctional gas distributor which may be located close to and may be connected directly to the counterlungs of the rebreather. Advantageously, gas distributor, counterlungs and scrubber may be worn on the back or the front of a diver close to the lung centroid.

According to an exemplary embodiment of the invention, a gas distributor being operable in closed circuit and open circuit mode is thus provided. Such a gas distributor may comprise an inhale chamber with one port to connect an inhale hose leading to a simple mouthpiece with direction valves. Another port of the inhale chamber may connect to an inhale counterlung which can be closed, for instance with a first spring loaded valve which may be denoted as inhale valve. A gas supply valve may be connected as well to the inhale chamber and may function as "on demand" valve. For example, such a gas supply valve may be composed of a diaphragm and a valve element with a lever. Furthermore, the gas distributor may comprise an exhale chamber having one port for connection to an exhale hose coming from the exhale side of a simple mouthpiece. Another port of the exhale chamber may connect to an exhale counterlung which can be closed with an exhale valve, such as a second spring loaded valve. Furthermore, the exhale chamber may be connected with an overpressure valve for releasing gas into the environment. Furthermore, the gas distributor may have integrated therein a switch which may be switchable by a user between an open circuit state and a closed circuit switch state.

In the closed circuit state, the user may be enabled to inhale breathing gas via the mouthpiece with (or and) an inhale direction valve, the inhale hose, the inhale chamber of the gas distributor, the inhale counterlung (if present), and the scrubber, and may be enabled to exhale breathing gas through the mouthpiece with (or and) an exhale direction valve, the exhale hose, the exhale chamber of the gas distributor, the exhale counterlung (if present), and the scrubber. For example, the overpressure valve may open beyond a first threshold pressure in the closed circuit state (particularly may open only when an overpressure in the exhale chamber of the gas distributor exceeds the first threshold pressure). Furthermore, the gas supply or "on demand" valve may function as automatic loop volume valve (ALV). For instance, the gas supply valve may provide gas beyond a second threshold pressure in the closed circuit state, which may also be denoted as a cracking pressure (particularly may open only when the absolute value of a negative pressure in an interior of the inhale chamber exceeds the second threshold pressure).

In the open circuit switch state, a user may be enabled to inhale breathing gas through the mouthpiece with (or and) the inhale direction valve, the inhale hose and the inhale chamber of the gas distributor with the gas supply valve (but not through the inhale counterlung (if present) and not through the scrubber). Furthermore, the user may be enabled in the open circuit switch state to exhale breathing gas through the mouthpiece with (or and) the exhale direction valve, the exhale hose and the exhale chamber of the gas distributor (but not through the exhale counterlung (if present) and not through the scrubber). In the open circuit switch state, the overpressure valve may be deactivated or the absolute value of the first threshold pressure may be reduced (particularly the overpressure valve may be converted into a configuration in which the first threshold pressure has a smaller value, i.e. opens already at a smaller overpressure value). In the open circuit switch state, the mentioned deactivation or down-regulation of the overpressure valve and hence its conversion to temporarily function as an outlet valve may be the direct result of the switching actuation of the switch. Moreover, the gas supply valve may provide gas in the open circuit switch state beyond a third threshold pressure with may also denoted as a further cracking pressure (in particular may open only when the absolute value of a negative pressure in an interior of the mouthpiece exceeds the third threshold pressure). The third threshold value may have a smaller absolute value than the second threshold pressure (in particular, the threshold or barrier against the supply of fresh diluent gas or breathing gas may be higher in the closed circuit mode than in the open circuit mode).

According to an embodiment, a gas distributor for a breathing apparatus is provided, which includes an open circuit and a closed circuit mode, a gas supply valve and an overpressure valve. The gas supply valve may be configured to allow the addition of gas at two different threshold pressure values in the closed circuit mode and in the open circuit mode. In the open circuit mode, fresh gas may be delivered already when a user generates a very small negative pressure in the inhale chamber of the gas distributor by inhaling (in OC mode, the loop may be isolated from the user). In closed circuit mode, fresh gas may be delivered only when the counterlungs are empty and the user generates a higher negative pressure in the loop by inhaling. Moreover, such an embodiment may use an overpressure valve with this function only in the closed circuit mode, whereas in the open circuit mode the overpressure valve may be actuated so as to be open, therefore not functioning as an outlet valve.

Alternatively, the overpressure valve may be designed with two different threshold pressure values, one higher pressure for CCR mode and one lower threshold pressure value for OC mode, in order to avoid a separate exhaust valve.

In an embodiment, in the closed circuit mode, a user is enabled to inhale gas via the mouthpiece, the inhale hose, the inhale chamber (and, if present, the inhale counterlung) and is enabled to exhale gas via the mouthpiece, the exhale hose, the exhale chamber (and, if present, the exhale counterlung). A scrubber may be connected between the inhale counterlung and the exhale counterlung and may thus also form part of the closed loop.

In an embodiment, in the open circuit mode, a user is enabled to inhale gas via the mouthpiece, the inhale hose and the inhale chamber (without the inhale counterlung, if present), and is enabled to exhale gas via the mouthpiece, the exhale hose and the exhale chamber (without the exhale counterlung, if present). Counterlungs and scrubber may be excluded from the gas path in the open circuit mode.

In an embodiment, the switch is accessible to a user for being switched by the user when wearing the rebreather for selecting the open circuit mode (in particular by pushing the switch into the gas distributor housing) or the closed circuit mode (in particular by pulling the switch out of the gas distributor housing). Operating the switch with a simple push-pull-logic is intuitive and failure robust for a user.

In an embodiment, the switch comprises an actuator body, in particular a triangular plate, configured for opening the inhale valve and the exhale valve (preferably simultaneously) when the switch is actuated so that a broad, broadest or broadened portion of the actuator body displaces the inhale valve and the exhale valve outwardly. For instance, a grip or a handle of the switch may be rigidly connected with such an actuator body so that the mechanical force exerted on the grip or handle may be transferred directly to the actuator body. The actuator body, in turn, may then actuate the inhale valve and the exhale valve, for instance by overcoming a biasing force (for instance generated by a respective spring or an array of magnets) biasing the inhale valve and the exhale valve into a normally closed condition. A mechanically very simple embodiment of the actuator body is a configuration with a broader portion and a narrower portion, which may be brought in interaction with the inhale valve and the exhale valve by a mere actuation of the switch. In particular a triangular configuration of the actuator body has turned out to be advantageous.

In an embodiment, the switch is a slider, i.e. a switch being operable by a user by sliding the switch into or out of a gas distributor housing. However, other configurations of the switch are possible, such as a rotatable switch, a pivotable switch, a lever switch, or an electronic switch connected with an electric actuator such as an electric motor.

In an embodiment, the gas distributor comprises a remote operation mechanism mechanically connected with the switch and configured for actuating the switch from a remote position. Advantageously, the switch of the gas distributor may be operated remotely, for instance with a Bowden wire, pneumatically or electrically with a servo magnet or an electromagnet. This may be advantageous in particular in a scenario in which the rebreather with the gas distributor is worn on the back of the diver where the switch of the gas distributor may be anatomically difficult to reach for a user.

In an embodiment, the overpressure valve is biased in a closed state (for instance by a biasing element such as a mechanical spring or an array of magnets) and is configured to be opened by overpressure in the exhale chamber for exhausting air into an environment of the rebreather. This may ensure that gas is only removed out of the rebreather when a certain overpressure value has been reached.

In an embodiment, the overpressure valve comprises a cap covering a gas passage and comprises a biasing element (for example a mechanical spring or an array of magnets) biasing the cap to cover the gas passage in a closed state. Thus, the cap may cover a gas passage such as a small tubular element or a tube with a sealing thereon. A biasing element, in particular a spring, may bias the cap to cover the gas passage in the closed circuit switch state so as to open only beyond a predefined threshold pressure to thereby execute its overpressure protection function. In particular, the biasing element may be connected between the cap and the switching axis, preferably by a lever of the switch, so that, upon switching into the open circuit switch state, the biasing force may be released (or reduced) from the cap. Therefore, an axis or axis element which can be set in either open circuit or closed circuit position, may pull in the closed circuit position a cap against a sealed seat to achieve an overpressure valve, which opens at an adjustable value. In the closed circuit position said cap may be released, the overpressure valve may open, and this opening may serve together with a one way valve as exhaust valve. In other words, this opening of the overpressure valve may correspond to its deactivation in the open circuit mode.

In an embodiment, the overpressure valve is biased in a closed state and is configured to be opened by overpressure exceeding a first threshold value in the closed circuit mode. In particular, the overpressure valve may be configured so that the first threshold value is in a range from 10 mbar to 50 mbar. Thus, the overpressure valve may be configured to open in the closed circuit switch state in the presence of an overpressure in a range from about 10 mbar to about 50 mbar as the first threshold pressure.

In an embodiment, the gas supply valve is biased in a closed state and is configured to be opened by a negative pressure exceeding a second threshold value in the closed circuit mode. Hence, also the gas supply valve may be in a normally closed mode which has to be actively overcome by at least a certain negative pressure in the inhale chamber acting on the gas supply valve for initiating supply of fresh gas. In particular, the gas supply valve may be configured so that the second threshold value is in a range from −3 mbar to −30 mbar. Thus, the "on demand" valve may be configured to provide gas in the closed circuit switch state in the presence of a relatively large negative pressure in a range from about −3 mbar to about −30 mbar as the second threshold pressure. Therefore, unwanted addition of diluent gas resulting from minor negative pressure in the loop may be prevented in the closed circuit mode by adjusting the cracking pressure to a relatively high value.

In an embodiment, the overpressure valve is configured to be opened already below the first threshold value in the open circuit mode. Hence, a relatively high threshold value must be exceeded to open the overpressure valve in the closed circuit mode in which gas circulates within the rebreather. In contrast to this, a lower pressure value may be sufficient to open the overpressure valve in the open circuit mode, in which a larger gas exchange may occur.

In an embodiment, the gas supply valve is configured to be opened by a negative pressure exceeding a third threshold value having a smaller absolute value than the second threshold value in the open circuit mode. In other words, already a smaller negative pressure in the inhale chamber may be sufficient for triggering fresh gas supply in the open circuit mode compared with the closed circuit mode.

In an embodiment, the gas supply valve is configured so that the third threshold value is in a range from −0.1 mbar to −3 mbar. Hence, the "on demand" valve may be configured to provide gas in the open circuit switch state already in the presence of a relatively small negative pressure in a range from about −0.1 mbar to about −3 mbar. Therefore, the user does not have to exert a high breathing work in the open circuit mode so that already a relatively small negative pressure may be sufficient to trigger the addition of gas.

In an embodiment, the gas supply valve comprises a threshold value adjusting spring and a lever and is configured to be loaded by the threshold value adjusting spring cooperating with the lever to adjust the third threshold value to have a smaller absolute value than the second threshold value. In an embodiment, the cracking pressure threshold adjustment mechanism can be realized by applying a counter force on the lever of a downstream valve with an elongation spring, which acts against the force exerted by a diaphragm on that lever. In an embodiment, the gas supply valve comprises said diaphragm, wherein the threshold value adjusting spring is configured to act against a force exerted by the diaphragm on the lever. One end of the threshold value adjusting spring may be connected movable with the above mentioned actuator body (for instance a triangular plate), whereas the other end of the threshold value adjusting spring may be connected with the lever. Operating the switch may thus allow to simultaneously modify the biasing state of the spring to thereby change the negative pressure threshold value at which the gas supply valve opens.

In an embodiment, the gas distributor comprises a purge button (which may be arranged in particular on the diaphragm) enabling a user to apply pressure on the diaphragm for actuating the gas supply valve to activate a manually triggered gas addition. Hence, the gas distributor may comprise a purge button, which enables the user to press manually on the diaphragm, thus configured for actuating the "on demand" valve to thereby activate a manual gas addition. The provision of such a purge button extends the flexibility of the user to configure the gas distributor in accordance with user preferences as well as clear inhale chamber, inhale hose, mouthpiece, exhale hose and exhale chamber from water.

In an embodiment, the gas distributor comprises an inhale valve biased (for instance by a biasing element such as a spring or a magnet array) for closing the first inhale port. Thus, in the open circuit switch state, the inhale valve may close the port of the inhale chamber to the inhale counterlung or to a scrubber.

In an embodiment, the inhale valve is biased for closing the first inhale port by a spring loaded mechanism acting along an axis element of the inhale valve. For example, the valve to close the first inhale port of the inhale chamber to the inhale counterlung or directly to a scrubber may be formed by a plate with a sealing, which in open circuit switch state is pressed and spring loaded against the opening from the first inhale port.

In an embodiment, the inhale valve may be configured for opening the first inhale port when a negative pressure in the inhale counterlung exceeds a fourth threshold value. Preferably, the fourth threshold value may be in a range from −10 mbar to −1 bar. The inhale valve, which may be configured to close the first inhale port of the inhale chamber to the inhale counterlung, and which is pressed and spring loaded against the opening of the first inhale port in the open circuit mode, can open, when a negative pressure inside the inhale counterlung exceeds a negative fourth threshold pressure level. This may ensure that also in the open circuit mode the automatic loop volume valve (ALV) function may be functional. This may prevent, in turn, a damage of rebreather components in the event that the user descends while operating the rebreather in the OC mode.

In an embodiment, the inhale valve for closing the first inhale port from the inhale chamber of the gas distributor to the inhale counterlung or to the scrubber may be opened in the closed circuit switch state. This may switch the inhale counterlung and the scrubber, or only the scrubber, into the gas path in the closed circuit switch state.

In an embodiment, the axis element of the inhale valve has a diameter in a range from 1 mm to 6 mm. Advantageously, the mentioned axis element may have very small dimensions which promotes a compact configuration of the gas distributor. Hence, the inhale valve for closing the first inhale port from the inhale chamber of the gas distributor to the inhale counterlung or to a scrubber may be opened mechanically in the closed circuit switch state by moving an axis element in axial direction, wherein the axis element preferably has a diameter between 1 mm and 6 mm.

In an embodiment, the gas distributor comprises an exhale valve biased for closing the first exhale port. Thus, the exhale valve may close the first exhale port of the exhale chamber to the exhale counterlung or to the scrubber, in the open circuit switch state.

In an embodiment, the exhale valve is biased for closing the first exhale port by a spring loaded mechanism acting along an axis element of the exhale valve. Preferably, the exhale valve configured to close the first exhale port of the exhale chamber to the exhale counterlung or to a scrubber may be formed by a plate with a sealing, which in the open circuit switch state is pressed and spring loaded against the opening from the first exhale port.

In an embodiment, the exhale valve is configured for opening the first exhale port when a negative pressure in the exhale counterlung exceeds a fifth threshold value. Preferably, the fifth threshold value is in a range from −10 mbar to −1 bar. Thus, the exhale valve configured to close the first exhale port of the exhale chamber to the exhale counterlung, which in the open circuit mode is pressed and spring loaded against the opening of the first exhale port, can open, when the negative pressure inside the exhale counterlung exceeds a negative fifth threshold pressure level, which may be preferably between −10 mbar and −1 bar.

Further preferably, the absolute value of the negative fifth threshold pressure level may be set to a higher level than the absolute value of the negative fourth threshold pressure level of the inhale valve for closing the inhale port of the inhale chamber to the inhale counterlung. This may ensure that also in the open circuit mode, the automatic loop volume valve (ALV) function is functional, thereby reliably preventing a damage of rebreather components in the event that the user descends while operating the rebreather in the OC mode.

In an embodiment, the exhale valve for closing the first exhale port from the exhale chamber of the gas distributor to the exhale counterlung or to the scrubber is opened in the closed circuit switch state.

In an embodiment, the axis element of the exhale valve has a diameter in a range from 1 mm to 6 mm. Advantageously, the mentioned axis element may have very small dimensions which promotes a compact configuration of the gas distributor. Hence, the exhale valve for closing the first exhale port from the exhale chamber of the gas distributor to the exhale counterlung may be opened mechanically in the closed circuit switch state by moving an axis element in axial direction, wherein the axis element preferably has a diameter between 1 mm and 6 mm.

In an embodiment, the rebreather comprises an inhale counterlung connected with the first inhale port of the gas distributor. Such an inhale counterlung on the inhale side may allow the loop to expand and contract when the user breathes.

In an embodiment, the first exhale port is directly (i.e. without an exhale counterlung in between) connected to an inlet of a scrubber. Since no exhale counterlung is provided in such an embodiment, the rebreather can be formed in a highly compact way. In such an embodiment, the rebreather may be provided with a single counterlung only, which is located on the inhale side, but without an exhale counterlung. The first exhale port of the gas distributor to the exhale counterlung may be instead of this connected to the inlet of the scrubber.

In another embodiment, the rebreather comprises an exhale counterlung connected with the first exhale port of the gas distributor. Such an exhale counterlung on the exhale side may allow the loop to expand and contract when the user breathes.

In an embodiment, the first inhale port is directly (i.e. without an inhale counterlung in between) connected to an outlet of a scrubber. Since no inhale counterlung is provided in such an embodiment, the rebreather can be formed in a highly compact way. In such an embodiment, the rebreather may be equipped with a single counterlung only, which is located on the exhale side, but without an inhale counterlung. Consequently, the first inhale port of the gas distributor to the inhale counterlung is instead connected to the outlet of the scrubber.

In an embodiment, the rebreather comprises a scrubber connected between the inhale counterlung or the first inhale port on the one hand and the exhale counterlung or the first exhale port on the other hand. Such a scrubber may remove carbon dioxide from exhaled gas, may add oxygen, and may thus prepare the gas for a next cycle or loop to be inhaled by a user.

In an embodiment, the rebreather comprises an inhale hose connected with the second inhale port. Correspondingly, the rebreather may comprise an exhale hose connected with the second exhale port. Moreover, the rebreather may comprise a mouthpiece connected between the inhale hose and the exhale hose. Advantageously, the mouthpiece may be embodied as simple and lightweight mouthpiece without the necessity of providing additional functionality apart from connections to the hoses and an anatomical adaptation to the jaw of a user, and preferably directional valves.

In an embodiment, the rebreather comprises an inhale direction valve connecting the mouthpiece and the inhale hose and/or an exhale direction valve connecting the mouthpiece and the exhale hose. Such an inhale direction valve may be a check valve allowing a gas flow from the gas distributor through the inhale hose into the mouthpiece, but not in the opposite direction. Correspondingly, an exhale direction valve may be a check valve allowing a gas flow from the mouthpiece into the exhale hose and into the gas distributor, but not in the opposite direction. The anatomical inhale-exhale sequence of the user may then automatically allow to operate the rebreather correctly. The inhale direction valve and/or the exhale direction valve may be integrated in the mouthpiece, or may be provided separately. In embodiment, it is also possible that the mouthpiece is embodied as dive surface valve having a closure mechanism.

In an embodiment, the rebreather is configured as one of the group consisting of a diving rebreather, a firefighting rebreather, an industrial rebreather, a military rebreather, and a medical rebreather. Other applications are possible as well.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

DETAILED DESCRIPTION OF THE DRAWINGS

Figure 1:
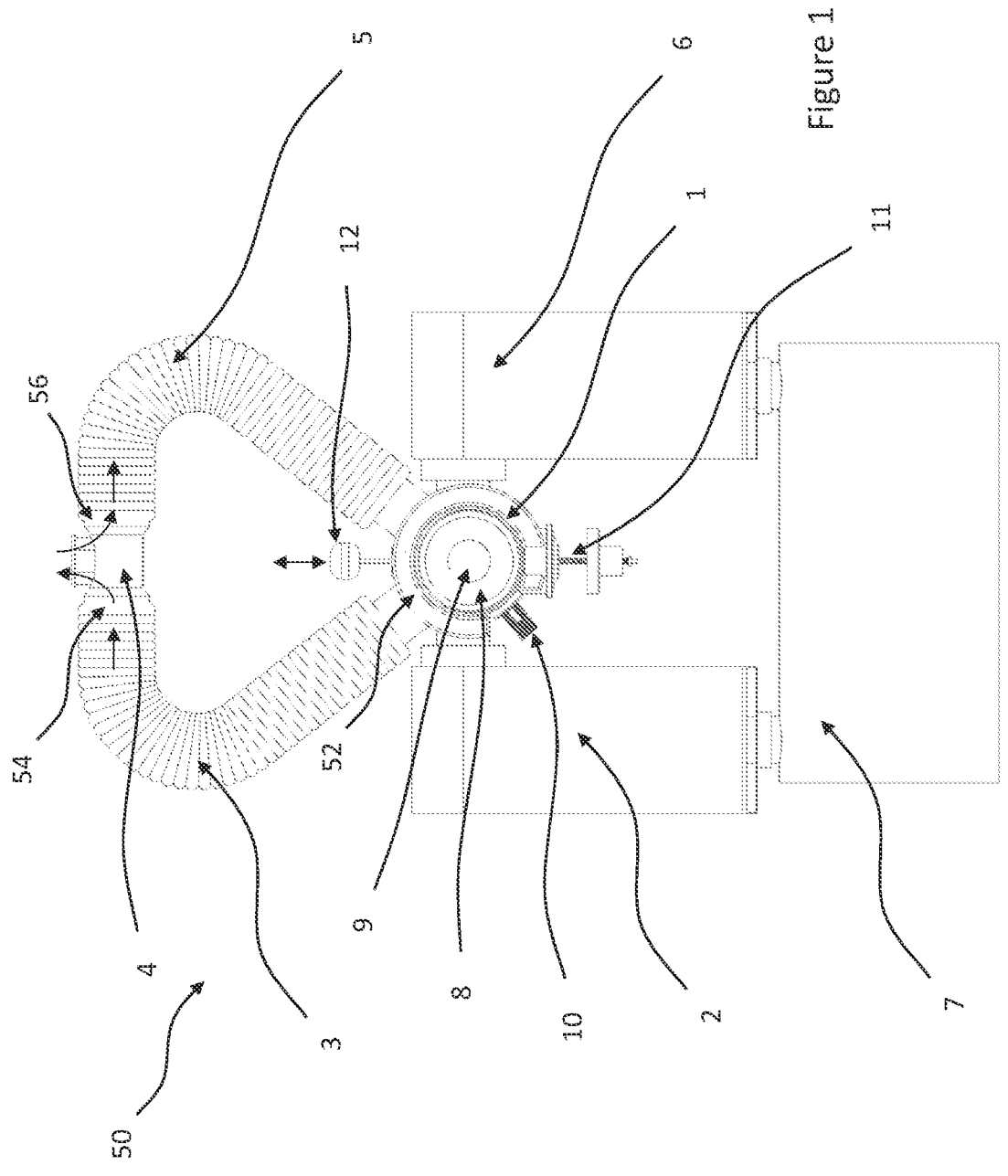
FIG. 1 illustrates a rebreather with a gas distributor according to an exemplary embodiment of the invention.

The illustration in the drawing is schematical. In different drawings, similar or identical elements are provided with the same reference signs.

Before, referring to the drawings, exemplary embodiments will be described in further detail, some basic considerations will be summarized based on which exemplary embodiments of the invention have been developed.

According to an exemplary embodiment of the invention, a gas distributor is provided which comprises an inhale chamber with a first inhale port to an inhale counterlung or (if no inhale counterlung is provided) directly to a scrubber, a second inhale port leading to an inhale hose, and a gas supply valve (which may also be denoted as an "on demand" valve). The gas distributor may further comprise an exhale chamber with a first exhale port to an exhale counterlung or (if no exhale counterlung is provided) directly to a scrubber, a first exhale port to an exhale hose coming from the exhale side of a mouthpiece, and an overpressure valve. Advantageously, the gas distributor can be switched between an open circuit mode and a closed circuit mode of a corresponding rebreather by a switch arranged at the gas distributor. Such a configuration allows to provide a mouthpiece in a simple and lightweight way which increases the operator convenience and reduces the risk of carbon dioxide accumulation in a large dead volume of a conventional complex mouthpiece providing a switching function.

Exemplary embodiments of the invention provide a gas distributor for a rebreather located close to the counterlung(s) and supporting both an open and a closed circuit mode. The gas distributor functions in combination with a simple mouthpiece assembly comprising a mouthpiece body, bite, direction valves, as well as exhale and inhale hose. Thus, it may be possible to achieve a lightweight and less bulky, hence more ergonomic solution in comparison to conventional rebreather mouthpieces with open circuit and closed circuit mode, where a second stage valve and a diaphragm have to be integrated into the mouthpiece.

A gas distributor according to an exemplary embodiment of the invention may make it possible to provide a rebreather in which a simple mouthpiece can be used, which has a small weight and is significantly less bulky than conventional bail out valves. Advantageously, a simple mouthpiece implemented in a rebreather according to an exemplary embodiment of the invention can be also provided with a very small dead space between the direction valves, so that the risk of an undesired carbon dioxide partial pressure buildup may be reduced.

As the gas distributor with automatic loop volume valve (ALV) function may be mounted directly to the counterlungs, the gas centroid of the counterlungs may be located closer to the diaphragm. Therefore, the cracking pressure can be set to a lower negative pressure, which results in lower physiological effort to overcome the cracking pressure.

Conventional rebreathers are designed with counterlungs located close to the lung centroid to minimize hydrostatic imbalance. As a gas distributor according to an exemplary embodiment of the invention with integrated ALV may be connected directly to the counterlung(s), the diaphragm may be also located closer to the lung centroid. Thus, the body position may have less impact on the required physiological effort to overcome the cracking pressure.

A further advantage of a gas distributor according to an exemplary embodiment of the invention is that moving parts of the switching mechanism may have an axis with a very small diameter, preferably between 1 mm and 6 mm, and can be sealed with small O-rings. This results in less friction and less actuation force in comparison to that of conventional rebreathers with large O-rings.

According to a preferred embodiment of the invention, the decoupling or isolation of rebreather components including counterlungs and scrubber may be achieved with spring loaded valves closing—in an OC mode—the ports connecting the gas distributor to the counterlungs and/or the scrubber. When the diver descends in OC mode, the counterlungs may collapse and the pressure inside the counterlungs and scrubber may become less than the ambient pressure. While in conventional BOVs with integrated ALV, the ALV is not functional in OC mode, the ALV in a gas distributor according to an exemplary embodiment of the invention may be also functional in OC mode: As soon as the negative pressure in the counterlungs overcomes the force from the springs on the closing valves, gas can pass the valves. Preferably, the spring force on the inhale valve for the first inhale port on the inhale side of the gas distributor may be set to a lower value than that of the exhale valve on the exhale side. This may ensure that the inhale valve on the inhale side opens first.

Figure 2:
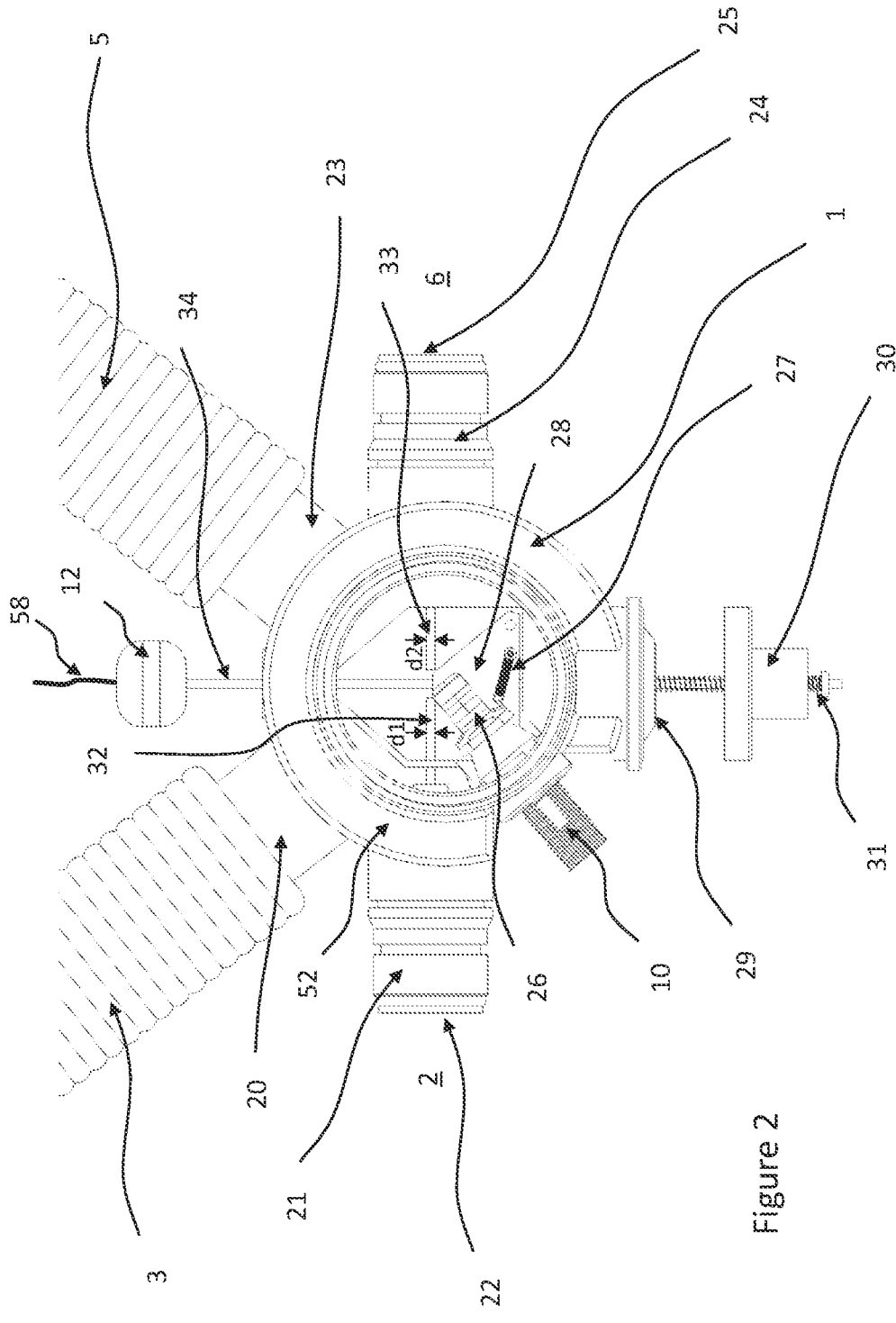
FIG. 2 illustrates a detailed view of the gas distributor of the rebreather of FIG. 1 in an open circuit state.
Figure 3:
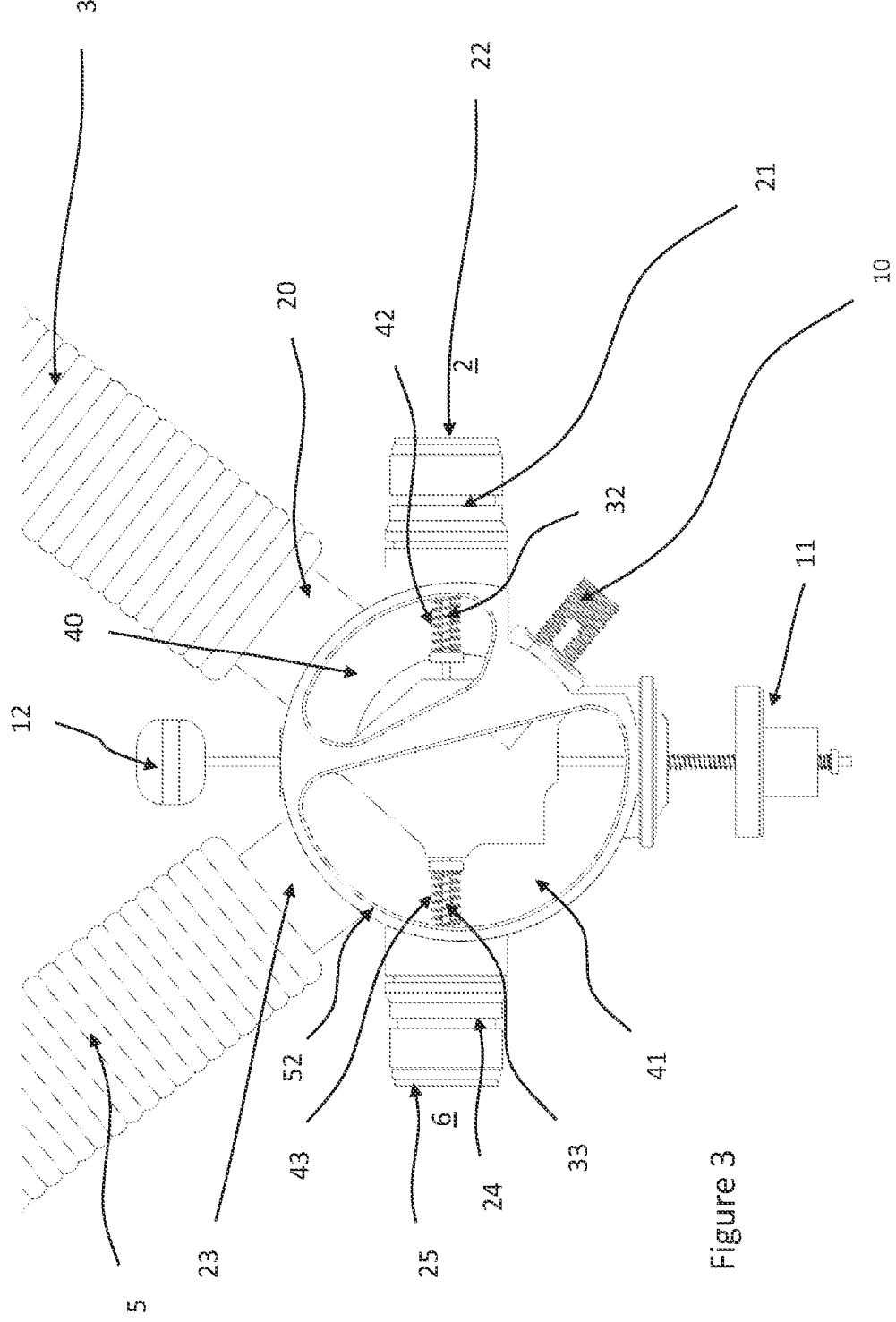
FIG. 3 illustrates a detailed view of a backside of the gas distributor of FIG. 1 in the open circuit state.
Figure 4:
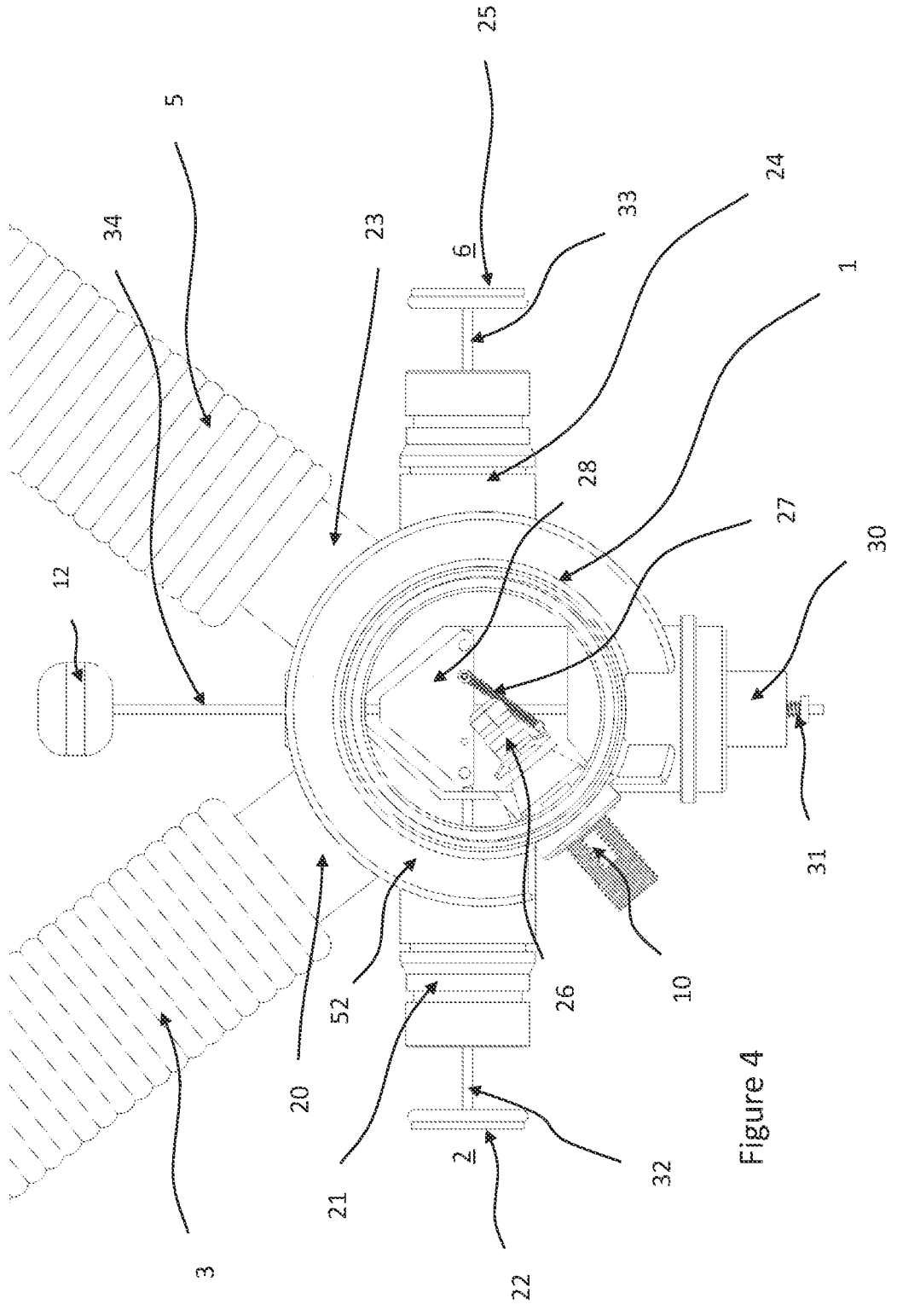
FIG. 4 illustrates a detailed view of the gas distributor of FIG. 1 in a closed circuit state.
Figure 5:
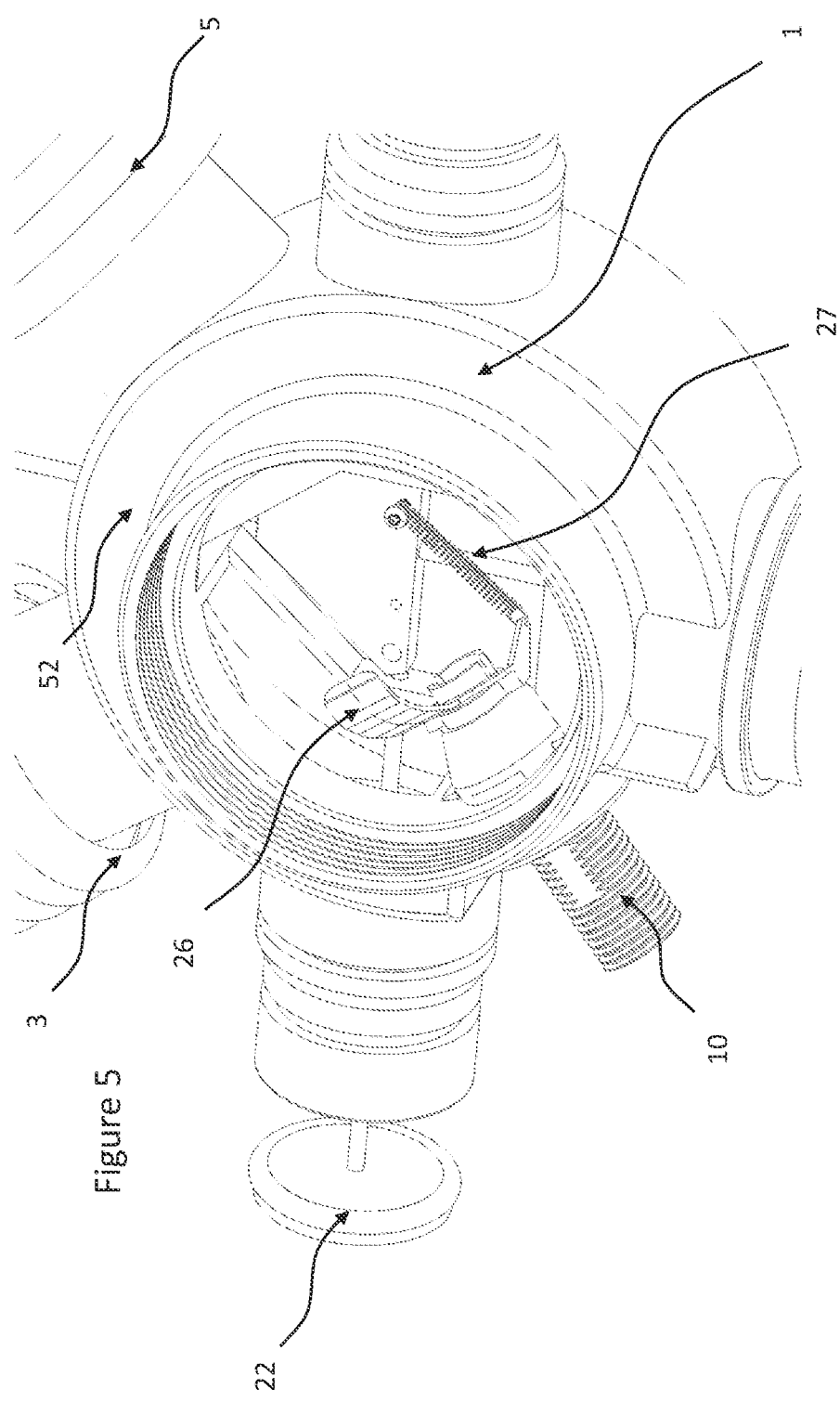
FIG. 5 illustrates details of a gas supply valve of the gas distributor of FIG. 1.

FIG. 1 illustrates a diving rebreather 50 with a gas distributor 1 according to an exemplary embodiment of the invention. FIG. 2 illustrates a detailed view of the gas distributor 1 of FIG. 1 in an open circuit (OC) state. FIG. 3 illustrates a detailed view of a backside of the gas distributor 1 of FIG. 1 in the open circuit (OC) state. FIG. 4 illustrates a detailed view of the gas distributor 1 of FIG. 1 in a closed circuit rebreather (CCR) state. FIG. 5 illustrates details of a gas supply valve 10 of the gas distributor 1 of FIG. 1.

FIG. 1 shows an overview of the rebreather 50 for supplying a user with breathing gas. As shown, the rebreather 50 comprises a gas distributor 1 which is directly connected with an inhale counterlung 2, an exhale counterlung 6, and inhale hose 3 and an exhale hose 5. Moreover, the gas distributor 1 is indirectly connected—by inhale hose 3 and exhale hose 5—with a mouthpiece 4. Hence, the mouthpiece 4 is connected between the inhale hose 3 and the exhale hose 5. Furthermore, the gas distributor 1 is indirectly connected—by inhale counterlung 2 and exhale counterlung 6—to a scrubber 7. In other words, scrubber 7 is connected between the inhale counterlung 2 and the exhale counterlung 6.

Now referring to FIG. 2 to FIG. 4, the inhale counterlung 2 is connected with a first inhale port 21 of the gas distributor 1. Furthermore, the exhale counterlung 6 is connected with a first exhale port 24 of the gas distributor 1. Beyond this, the inhale hose 3 is connected with a second inhale port 20 of the gas distributor 1. Correspondingly, the exhale hose 5 is connected with a second exhale port 23 of the gas distributor 1.

As shown schematically in FIG. 1, the rebreather 50 comprises an inhale direction valve 54, which is embodied as a unidirectional gas valve, arranged for connecting the mouthpiece 4 and the inhale hose 3. Furthermore, an exhale direction valve 56, which is embodied as a further unidirectional directional gas valve, is located for connecting the mouthpiece 4 and the exhale hose 5. It is possible that the direction valves 54, 56 form part of the mouthpiece 4. Alternatively, the direction valves 54, 56 may be provided separately from the mouthpiece 4.

During use, a user may wear the rebreather 50 so that a below described switch 12 of the gas distributor 1 is located at a chest or at a back of the user. When located at the chest of the user, the user may conveniently actuate switch 12 by hand. For simplifying operation of switch 12 when the user wears the rebreather 50 at her or his back, the gas distributor 1 may be equipped with a remote operation mechanism 58 (such as a Bowden wire), see FIG. 2. The remote operation mechanism 58 may be mechanically connected with the switch 12 and may be configured for actuating the switch 12 by the user from a remote position.

As best seen in FIG. 2, FIG. 3 and FIG. 4, gas distributor 1 is configured for gas connection with inhale hose 3 and with exhale hose 5 with mouthpiece 4 in between (see FIG. 1).

Referring in particular to FIG. 3, the gas distributor 1 comprises a gas distributor housing 52 in and on which the various constituents of the gas distributor 1 are arranged.

In particular, an inhale chamber 40 is formed at the gas distributor housing 52 and comprises a first inhale port 21 for connection with the inhale counterlung 2 (or directly with scrubber 7, for instance when inhale counterlung 2 is omitted, wherein such an embodiment is not shown in the figures). Moreover, inhale chamber 40 comprises a second inhale port 20 for gas connection with the inhale hose 3. A gas supply valve 10 of the inhale chamber 40 serves for supplying fresh gas (such as air from a gas bottle, not shown) on demand and may thus also be denoted as "on demand" valve.

Furthermore, gas distributor 1 comprises an exhale chamber 41 at the gas distributor housing 52 which comprises, in turn, a first exhale port 24 for gas connection with an exhale counterlung 6 (or directly with scrubber 7, for instance when exhale counterlung 6 is omitted, wherein such an embodiment is not shown in the figures). Moreover, exhale chamber 41 comprises a second exhale port 23 for gas connection with the exhale hose 5. An overpressure valve 11 of exhale chamber 41 functions for opening towards an environment of the rebreather 50 in an event of overpressure.

Furthermore, the already mentioned switch 12 forms part of the gas distributor 1 and is arranged at (more precisely partially within and partially outside of) the gas distributor housing 52. Switch 12 is configured for being switchable by a user between an open circuit mode and a closed circuit mode. More specifically, the switch 12 is accessible to the user for being switched by the user for selecting the open circuit mode by pushing the switch 12 into the gas distributor housing 52 (compare FIG. 2 and FIG. 3). Moreover, a user can switch the switch 12 into the closed circuit mode by pulling the switch 12 out of the gas distributor housing 52 (compare FIG. 4). Such a switching logic is highly intuitive for a user.

In the closed circuit mode, the user is enabled to inhale gas via the mouthpiece 4, the inhale hose 3, the inhale chamber 40 and the inhale counterlung 2 and is enabled to exhale gas via the mouthpiece 4, the exhale hose 5, the exhale chamber 41 and the exhale counterlung 6. The scrubber 7 may also be within the closed gas loop according to the closed circuit mode.

In the open circuit mode, a user is enabled to inhale gas via the mouthpiece 4, the inhale hose 3 and the inhale chamber 40 without the inhale counterlung 2, and is enabled to exhale gas via the mouthpiece 4, the exhale hose 5 and the exhale chamber 41 without the exhale counterlung 6. Hence, the inhale counterlung 2, the exhale counterlung 6 and the scrubber 7 may be deactivated or without function in the open circuit mode.

Referring to the overpressure valve 11 of the exhale chamber 41 in further detail, overpressure valve 11 may be biased in a closed state. Moreover, overpressure valve 11 may be configured to be opened by overpressure in the exhale chamber 41 for exhausting air into an environment of the rebreather 50. For this purpose, the illustrated overpressure valve 11 comprises a cap 30 covering a gas passage and comprises a spring-type biasing element 31 biasing the cap 30 to cover the gas passage in a closed state. Due to this construction, the overpressure valve 11 can be biased in a closed state and can be opened by overpressure exceeding a first threshold value in the closed circuit mode. Preferably, the overpressure valve 11 is designed so that the first threshold value is in a range from 10 mbar to 50 mbar. However, the overpressure valve 11 may be further designed to be opened already below said first threshold value in the open circuit mode. Descriptively speaking, the overpressure valve 11 may open—for depressurizing the exhale chamber 41—already by a lower overpressure in the open circuit mode as compared to the closed circuit mode. For instance, overpressure valve 11 may open in the closed circuit mode only at a significant overpressure for pressure decrease or relief, while overpressure valve 11 may be quasi open in the open circuit mode or may open in the open circuit mode at a lower overpressure value compared to the closed circuit mode.

Now referring to the gas supply valve 10 of the inhale chamber 40, gas supply valve 10 may be biased in a closed state and may be configured to be opened by a negative pressure in the inhale chamber 40 exceeding a second threshold value in the closed circuit mode. Preferably, the gas supply valve 10 is designed so that the second threshold value is in a range from −3 mbar to −30 mbar. Furthermore, the gas supply valve 10 may be designed to be opened already by a negative pressure exceeding a third threshold value having a smaller absolute value than the second threshold value in the open circuit mode. Advantageously, the gas supply valve 10 may be designed so that the third threshold value is in a range from −0.1 mbar to −3 mbar. Descriptively speaking, the gas supply valve 10 may open—for supplying fresh gas to the inhale chamber—already by a negative pressure having a lower absolute value in the open circuit mode as compared to the closed circuit mode. In the closed circuit mode, gas supply valve 10 delivers additional gas only at a strong pressure drop, whereas the gas supply valve 10 delivers additional gas already at a lower pressure drop in the open circuit mode.

In order to provide this functionality and now referring to FIG. 2, FIG. 4 and FIG. 5, the gas supply valve 10 comprises a threshold value adjusting spring 27 and a lever 26. The gas supply valve 10 is designed to be loaded by the threshold value adjusting spring 27 cooperating with the lever 26 to adjust the third threshold value to have a smaller absolute value than the second threshold value. For this purpose, the gas supply valve 10 comprises a diaphragm 8 (as shown in FIG. 1). The threshold value adjusting spring 27 is config- ured to act against a force exerted by the diaphragm 8 on the lever 26.

Still referring to FIG. 1, the gas distributor 1 comprises a purge button 9 enabling a user to press manually on the diaphragm 8 for actuating the gas supply valve 10 to activate a manual gas addition. By taking this measure, a user may trigger supply of an extra amount of gas.

As best seen in FIG. 2 to FIG. 4, the gas distributor 1 comprises an inhale valve 22 which may be spring-biased for closing the first inhale port 21. More specifically, the inhale valve 22 may be biased for closing the first inhale port 21 by a spring loaded mechanism acting along an axis element 32 (see FIG. 2) of the inhale valve 22. Said axis element 32 or shaft may have a small diameter d1 in a range from 1 mm to 6 mm. This may ensure a compact design of the gas distributor 1.

Advantageously, the inhale valve 22 is configured for opening the first inhale port 21 when a negative pressure in the inhale counterlung 2 exceeds a fourth threshold value which is preferably selected in a range from −10 mbar to −1 bar. This may reliably prevent an excessive negative pres- sure in the inhale counterlung 2 by providing a pressure equilibration function triggered by exceeding a threshold value.

As best seen in FIG. 2 to FIG. 4 as well, the gas distributor 1 comprises an exhale valve 25 biased for closing the first exhale port 24. The exhale valve 25 may be biased for closing the first exhale port 24 by a spring loaded mecha- nism acting along an axis element 33 (see FIG. 2) of the exhale valve 25. Said axis element 33 or shaft may have a small diameter d2 in a range from 1 mm to 6 mm. This may ensure a compact design of the gas distributor 1.

Advantageously, the exhale valve 25 is configured for opening the first exhale port 24 when a negative pressure in the exhale counterlung 6 exceeds a fifth threshold value which is preferably selected in a range from −10 mbar to −1 bar. This may reliably prevent an excessive negative pres- sure in the exhale counterlung 6 by providing a pressure equilibration function triggered by exceeding a threshold value.

It may be preferred that the absolute value of the negative pressure corresponding to the fifth threshold value is higher than the absolute value of the negative pressure correspond- ing to the fourth threshold value. Hence, pressure equilibra- tion of the inhale counterlung 2 may start prior to pressure equilibration of the exhale counterlung 6. The described pressure equilibration function may ensure that inhale valve 22 and exhale valve 25 open in the event of excessive negative pressure in the counterlungs 2, 6, for instance when a user quickly dives downwardly in open circuit mode. This may prevent rebreather 50 from damage.

Descriptively speaking, inhale valve 22 and exhale valve 25 may be valves with a spring-loaded axis which pulls a spring plate against a valve seat.

Advantageously, the switch 12 may comprise an actuator body 28 which is here embodied as a triangular plate, as can be seen best in FIG. 2 and FIG. 4. Said actuator body 28 is configured for opening the inhale valve 22 and the exhale valve 25 when the switch 12 is actuated so that a broad, broadest or broadened portion of the actuator body 28 displaces the inhale valve 22 and the exhale valve 25 outwardly by moving their axis elements 32, 33 along their axial directions. Descriptively speaking, the preferably tri- angular actuator body 28 functions as a spring-biased valve plate being actuated by switch 12 for accomplishing a conversion between the open circuit mode of FIG. 2 and the closed circuit mode of FIG. 4. When the user pulls switch 12 upwardly, the preferably triangular actuator body 28 moves upwardly and thereby opens inhale valve 22 and exhale valve 25 by axially moving axis elements 32, 33 outwardly by actuator body 28. Descriptively speaking, a motion of actuator body 28 along a first direction (the vertical direction according to FIG. 2 and FIG. 4) causes a motion of the valve axis elements 32, 33 along a second direction (the horizontal direction according to FIG. 2 and FIG. 4) being perpendicu- lar to the first direction. More specifically, the motion of the valve axis elements 32, 33 is along the extension of their axes.

FIG. 1 details an exemplary embodiment of the rebreather 50. The gas distributor 1 thereof has inhale chamber 40 gas connected to inhale counterlung 2 and to inhale hose 3 leading to the inhale side of mouthpiece 4. Two direction valves 54, 56 are located inside the mouthpiece 4 or directly next to the mouthpiece 4. Exhale hose 5 is leading from the exhale side of the mouthpiece 4 to the exhale chamber 41 of the gas distributor 1. The exhale side of the gas distributor 1 is further connected to the exhale counterlung 6. The exhale side of the gas distributor 1 is equipped with the overpressure valve 11. Both counterlungs 2, 6 are connected to scrubber 7. An "on demand" valve is formed as down- stream or gas supply valve 10 with a connection to a first stage pressure regulator, diaphragm 8 and purge button 9. Gas supply valve 10 forms part of the inhale chamber 40 of the gas distributor 1. Switch 12 has an open circuit state and a closed circuit state. The assembly including gas distributor 1, counterlungs 2, 6 and scrubber 7 is preferably worn either on the chest or on the back of the diver.

FIG. 2 shows a detailed view of the gas distributor 1 where the switch 12 is in the open circuit state. To under- stand the mechanism of the gas distributor 1, the diaphragm 8 is not shown.

The inhale chamber 40 of the gas distributor 1 comprises first inhale port 21 to the inhale counterlung 2, second inhale port 20 to the inhale hose 3, and downstream or gas supply valve 10 with lever 26.

The exhale chamber 41 of the gas distributor 1 comprises first exhale port 24 to the exhale counterlung 6, second exhale port 23 to the exhale hose 5, and overpressure valve 11 composed of a direction valve 29, cap 30 and spring 31 to load that cap 30. In open circuit state, this cap 30 is lifted and the direction valve 29 functions as exhaust valve similar to that of an open circuit second stage.

First inhale port 21 leading to the inhale counterlung 2 is closed with inhale valve 22. First exhale port 24 leading to the exhale counterlung 6 is closed with exhale valve 25. Inhale valve 22 is actuated with axis element 32. Exhale valve is actuated with axis element 33.

A triangular plate functions as actuator body 28 and is sitting located on one common axis 34 together with the switch 12. Elongation spring 27 is not elongated and is axial to the movement axis of the lever 26, thus no force is applied on the lever 26 from the downstream valve 10 according to FIG. 2.

FIG. 3 shows the backside of the gas distributor 1 in open circuit state, where the cover of the back is removed.

First inhale port 21 leading to the inhale counterlung 2 is closed with inhale valve 22 which is actuated with axis elements 32. Compression spring 42 is used to load inhale valve 22 with the axis element 32, to achieve sealing of the first inhale port 21.

First exhale port 24 leading to the exhale counterlung 6 is closed with exhale valve 25 which is actuated with axis element 33. Compression spring 43 is used to load exhale valve 25 via axis element 33, to achieve sealing of the first exhale port 24.

FIG. 4 shows the gas distributor 1 in the closed circuit state. To understand the mechanism of the gas distributor 1, the diaphragm 8 is not shown.

The exhale chamber 41 of the gas distributor 1 comprises inter alia the overpressure valve 11 comprising direction valve 29, cap 30 and spring 31 to load cap 30. In closed circuit state this cap 30 is pressed with the compression spring 31 and axis element 34 on a seat and covers direction valve 29. The pressure of the overpressure valve 11 is determined by compression spring 31. The axis 34 also connects the switch 12 with the actuator body 28 being here embodied as triangular plate. In the closed circuit state, said actuator body 28 is pulled up, further pushing axis element 32 and axis element 33 apart, thereby opening inhale valve 22 leading to the inhale counterlung 2 and exhale valve 25 leading to the exhale counterlung 6.

In the closed circuit position according to FIG. 4, the elongation spring 27 is elongated in radial direction of the lever 26, thus applying a counter force on the lever 26, which leads to an increased cracking pressure of the "on demand" or gas supply valve 10 including lever 26 and diaphragm 9. In other words, the described mechanism ensures that an absolute value of the second threshold value corresponding to the closed circuit mode is larger than an absolute value of the third threshold value corresponding to the open circuit mode.

FIG. 5 details how the lever 27 of the downstream valve 10 is loaded with elongation spring 27 to achieve the increased negative cracking pressure in the closed circuit mode.

All axis elements (see in particular reference signs 32, 33, 34) may be sealed to avoid gas flow between the two chambers 40, 41 of the gas distributor 1 as well as to avoid water ingress. O-rings are not shown in the figures. More specifically, axis element 33 can be sealed, for instance using an O-ring, at a transition between the exhale chamber 41 and the inhale chamber 40. Also axis element 32 may have a corresponding sealing. Moreover, axis element 34 may be sealed, for instance using an O-ring, in order to avoid water entry.

Figure 6:
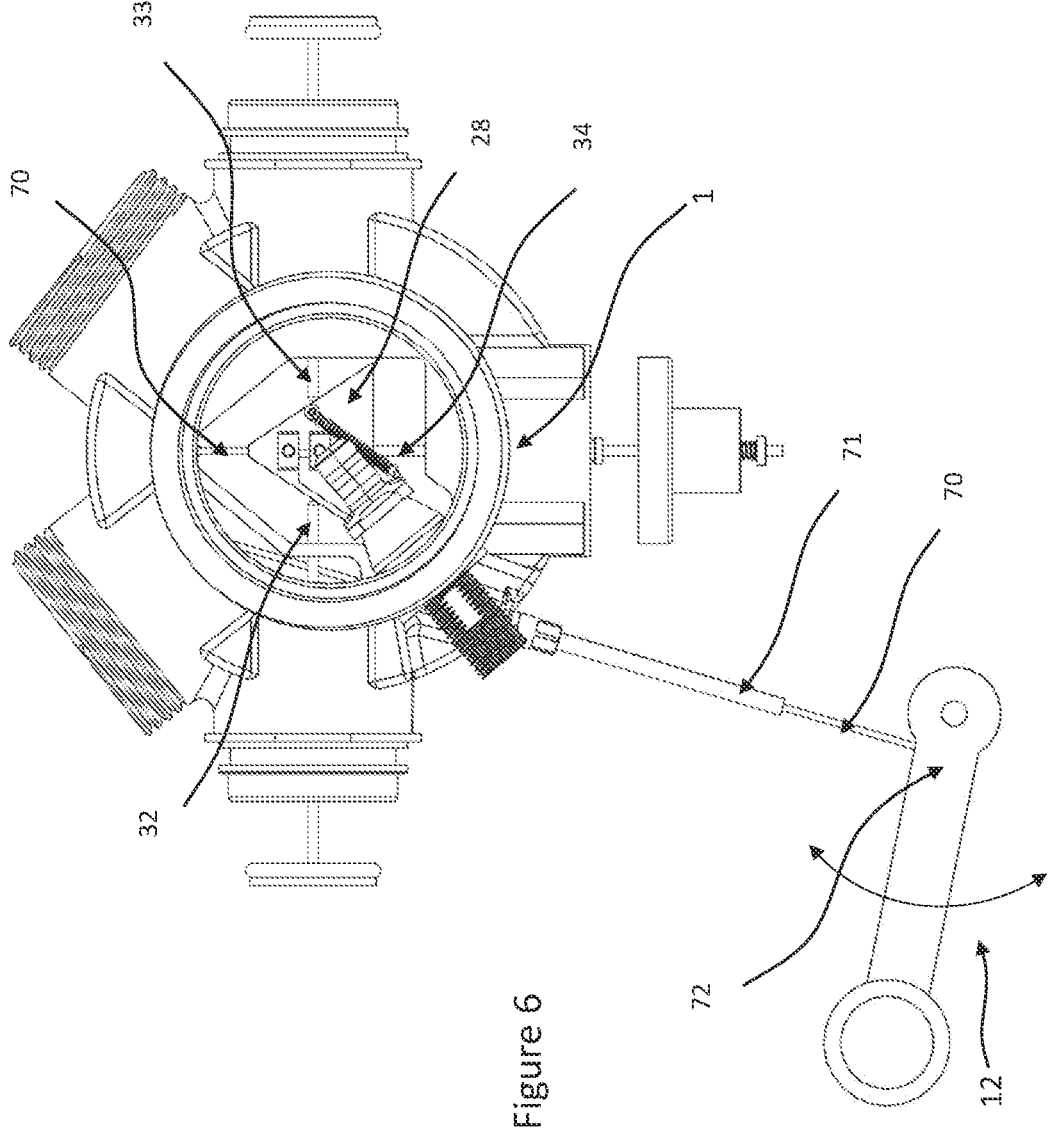
FIG. 6 illustrates part of a rebreather with a gas distributor according to another exemplary embodiment of the invention.
Figure 7:
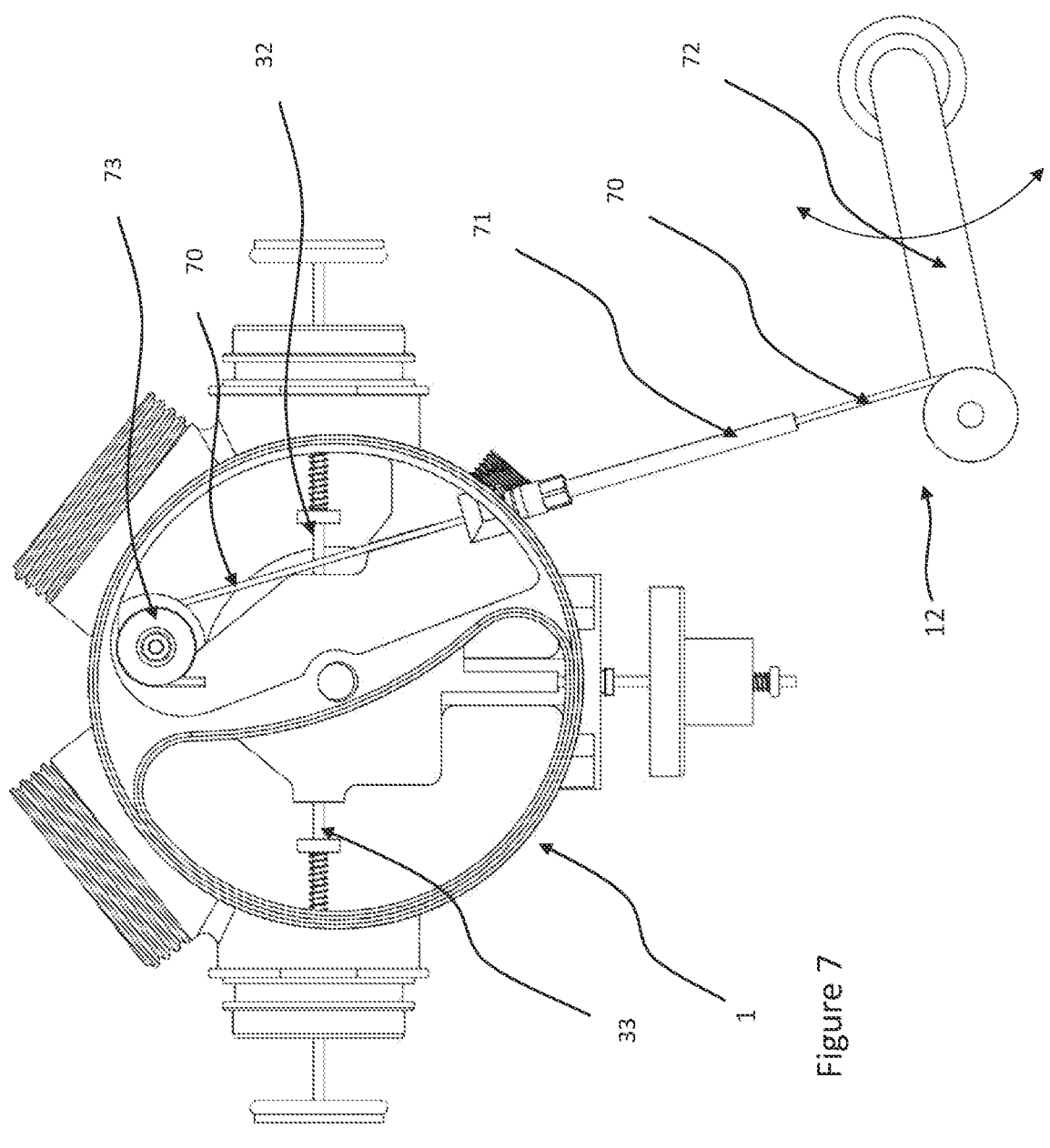
FIG. 7 illustrates another view of the part of the rebreather with the gas distributor according to FIG. 6.

FIG. 6 illustrates part of a rebreather 50 with a gas distributor 1 according to another exemplary embodiment of the invention. FIG. 7 illustrates another view of the part of the rebreather 50 with the gas distributor 1 according to FIG. 6. In the embodiment of FIG. 6 and FIG. 7, the switch 12 operates a Bowden cable 70, with which axis 34 and thus also the elements 28, 30, 31 may be actuated. Reference sign 71 denotes a cover of the Bowden cable 70. Furthermore, an operation lever 72 (i.e. a remote switch) is provided. Reference sign 73 shows a deflection roller.

The illustrations in the drawings are schematic. In different drawings, similar or identical elements are provided with the same reference signs.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

Implementation of the invention is not limited to the preferred embodiments shown in the figures and described above. Instead, a multiplicity of variants are possible which use the solutions shown and the principle according to the invention even in the case of fundamentally different embodiments.

The invention claimed is:

1. A gas distributor for a rebreather, the gas distributor being configured for connection with an inhale hose and with an exhale hose with a mouthpiece in between, wherein the gas distributor comprises:

a gas distributor housing;

an inhale chamber at the gas distributor housing and comprising a first inhale port for connection with an inhale counterlung or with a scrubber, a second inhale port for connection with the inhale hose, and a gas supply valve for supplying gas on demand;

an exhale chamber at the gas distributor housing and comprising a first exhale port for connection with an exhale counterlung or with the scrubber, a second exhale port for connection with the exhale hose, and an overpressure valve for opening in an event of overpressure;

a manual switch arranged at the gas distributor housing and configured for being switchable between an open circuit mode and a closed circuit mode;

and wherein the manual switch comprises an actuator body configured for opening an inhale valve, which closes the first inhale port, and for opening an exhale valve, which closes the first exhale port, when the manual switch is actuated so that the actuator body displaces the inhale valve and the exhale valve outwardly, wherein a grip or handle of the switch is connected to the actuator body so that a mechanical force exerted on the grip or handle is transferred directly to the actuator body;

wherein a first axis element connects the inhale valve to the actuator body, the first axis element comprises one end connected to the inhale valve and another end connected to the actuator body;

wherein a second axis element connects the exhale valve to the actuator body, the second axis element comprises one end connected to the exhale valve and another end connected to the actuator body;

wherein the actuator body is moved by the grip or handle to enlarge a distance between the one end of the first axis element and the one end of the second axis element such that the inhale valve and the exhale valve are moved outwardly in opposite directions to each other.

2. The gas distributor according to claim 1, comprising at least one of the following features:

comprising a remote operation mechanism mechanically connected with the manual switch and configured for actuating the manual switch from a remote position;

wherein in the closed circuit mode, a user is enabled to inhale gas via the mouthpiece, the inhale hose, the inhale chamber, optionally the inhale counterlung, and the scrubber, and is enabled to exhale gas via the mouthpiece, the exhale hose, the exhale chamber, optionally the exhale counterlung, and the scrubber;

wherein in the open circuit mode, a user is enabled to inhale gas via the mouthpiece, the inhale hose and the inhale chamber without the optional inhale counterlung, and without the scrubber, and is enabled to exhale gas via the mouthpiece, the exhale hose and the exhale chamber without the optional exhale counterlung, and without the scrubber;

wherein the manual switch is accessible to a user for being switched by the user when wearing the rebreather for selecting the open circuit mode by pushing the manual switch into the gas distributor housing, or the closed circuit mode by pulling the manual switch out of the gas distributor housing;

wherein the overpressure valve is biased in a closed state and is configured to be opened by overpressure in the exhale chamber for exhausting air into an environment of the rebreather;

wherein the overpressure valve comprises a cap covering a gas passage and comprises a biasing element biasing the cap to cover the gas passage in a closed state;

wherein the overpressure valve is biased in a closed state and is configured to be opened by overpressure exceeding a first threshold value in the closed circuit mode, wherein the overpressure valve is configured so that the first threshold value is in a range from 10 mbar to 50 mbar and/or wherein the overpressure valve is configured to be opened already below the first threshold value in the open circuit mode.

3. The gas distributor according to claim 1, wherein the gas supply valve is biased in a closed state and is configured to be opened by a negative pressure exceeding a second threshold value in the closed circuit mode, wherein the gas supply valve is configured so that the second threshold value is in a range from −3 mbar to −30 mbar.

4. The gas distributor according to claim 3, wherein the gas supply valve is configured to be opened by a negative pressure exceeding a third threshold value having a smaller absolute value than the second threshold value in the open circuit mode, wherein the gas supply valve is configured so that the third threshold value is in a range from −0.1 mbar to −3 mbar and/or wherein the gas supply valve comprises a threshold value adjusting spring and a lever and is configured to be loaded by the threshold value adjusting spring cooperating with the lever to adjust the third threshold value to have a smaller absolute value than the second threshold value.

5. The gas distributor according to claim 4, wherein the gas supply valve comprises a diaphragm, and wherein the threshold value adjusting spring is configured to act against a force exerted by the diaphragm on the lever.

6. The gas distributor according to claim 1, wherein the inhale valve is biased for closing the first inhale port.

7. The gas distributor according to claim 6, comprising at least one of the following features:

wherein the inhale valve is biased for closing the first inhale port by a spring loaded mechanism acting along the first axis element of the inhale valve, wherein the first axis element of the inhale valve has a diameter in a range from 1 mm to 6 mm;

wherein the inhale valve is configured for opening the first inhale port when a negative pressure in the inhale counterlung exceeds a fourth threshold value, wherein the fourth threshold value is in a range from −10 mbar to −1 bar.

8. The gas distributor according to claim 1, wherein the exhale valve is biased for closing the first exhale port.

9. The gas distributor according to claim 8, comprising at least one of the following features:

wherein the exhale valve is biased for closing the first exhale port by a spring loaded mechanism acting along the second axis element of the exhale valve, wherein the second axis element of the exhale valve has a diameter in a range from 1 mm to 6 mm;

wherein the actuator body is a triangular plate;

wherein a broad portion of the actuator body displaces the inhale valve and the exhale valve outwardly, when the manual switch is actuated for opening the inhale valve and the exhale valve;

wherein the exhale valve is configured for opening the first exhale port when a negative pressure in the exhale counterlung exceeds a fifth threshold value, wherein the fifth threshold value is in a range from −10 mbar to −1 bar.

10. A rebreather for supplying a user with breathing gas, wherein the rebreather comprises a gas distributor according to claim 1.

11. The rebreather according to claim 10, comprising the inhale counterlung connected with the first inhale port.

12. The rebreather according to claim 10, comprising the exhale counterlung connected with the first exhale port.

13. The rebreather according to claim 11, comprising the scrubber connected between the inhale counterlung or the first inhale port on the one hand and the exhale counterlung or the first exhale port on the other hand.

14. The rebreather according to claim 10, comprising the inhale hose connected with the second inhale port.

15. The rebreather according to claim 10, comprising the exhale hose connected with the second exhale port.

16. The rebreather according to claim 10, comprising the mouthpiece connected between the inhale hose and the exhale hose.

17. The rebreather according to claim 10, configured as one of the group consisting of a diving rebreather, a firefighting rebreather, an industrial rebreather, a military rebreather, and a medical rebreather.

18. A method of wearing a rebreather according to claim 10, wherein the user places the manual switch of the gas distributor at a chest or at a back of the user.

* * * * *